(12) United States Patent
Oiwa

(10) Patent No.: US 11,045,624 B2
(45) Date of Patent: Jun. 29, 2021

(54) MEDICAL ELONGATED BODY

(71) Applicant: TERUMO KABUSHIKI KAISHA, Tokyo (JP)

(72) Inventor: Tomoya Oiwa, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 268 days.

(21) Appl. No.: 15/928,586

(22) Filed: Mar. 22, 2018

(65) Prior Publication Data
US 2018/0326180 A1 Nov. 15, 2018

(30) Foreign Application Priority Data

May 10, 2017 (JP) .............................. JP2017-094095

(51) Int. Cl.
*A61M 25/00* (2006.01)
*A61M 25/09* (2006.01)

(52) U.S. Cl.
CPC .... *A61M 25/0023* (2013.01); *A61M 25/0043* (2013.01); *A61M 25/0045* (2013.01); *A61M 25/09* (2013.01); *A61M 25/09041* (2013.01); *A61M 2025/006* (2013.01); *A61M 2025/0046* (2013.01); *A61M 2025/0048* (2013.01); *A61M 2025/09133* (2013.01); *A61M 2205/0222* (2013.01); *A61M 2205/0238* (2013.01)

(58) Field of Classification Search
None
See application file for complete search history.

(56) References Cited

U.S. PATENT DOCUMENTS

| | | | |
|---|---|---|---|
| 2006/0079952 A1* | 4/2006 | Kaplan | A61F 2/97 623/1.11 |
| 2009/0246252 A1* | 10/2009 | Arps | A61L 29/085 424/425 |
| 2014/0188004 A1 | 7/2014 | Kanazawa et al. | |
| 2017/0007805 A1* | 1/2017 | Tsubooka | A61B 17/22 |
| 2018/0280666 A1* | 10/2018 | Yamazaki | A61B 17/12109 |
| 2019/0240461 A1* | 8/2019 | Dayton | A61M 25/09 |

FOREIGN PATENT DOCUMENTS

JP 2014-124408 A 7/2014

* cited by examiner

*Primary Examiner* — Etsub D Berhanu
*Assistant Examiner* — Aurelie H Tu
(74) *Attorney, Agent, or Firm* — Buchanan Ingersoll & Rooney PC

(57) ABSTRACT

Provided is an improved medical elongated body which can be inserted into a biological lumen and can be restrained from unintentionally moving at a target site inside the biological lumen. The medical elongated body includes a main body portion that extends in an axial direction, and a projection portion that protrudes radially outward on an outer circumference of the main body portion and extends in the axial direction. One surface of the projection portion in a circumferential direction has higher sliding properties than an other surface of the projection portion in the circumferential direction.

16 Claims, 11 Drawing Sheets

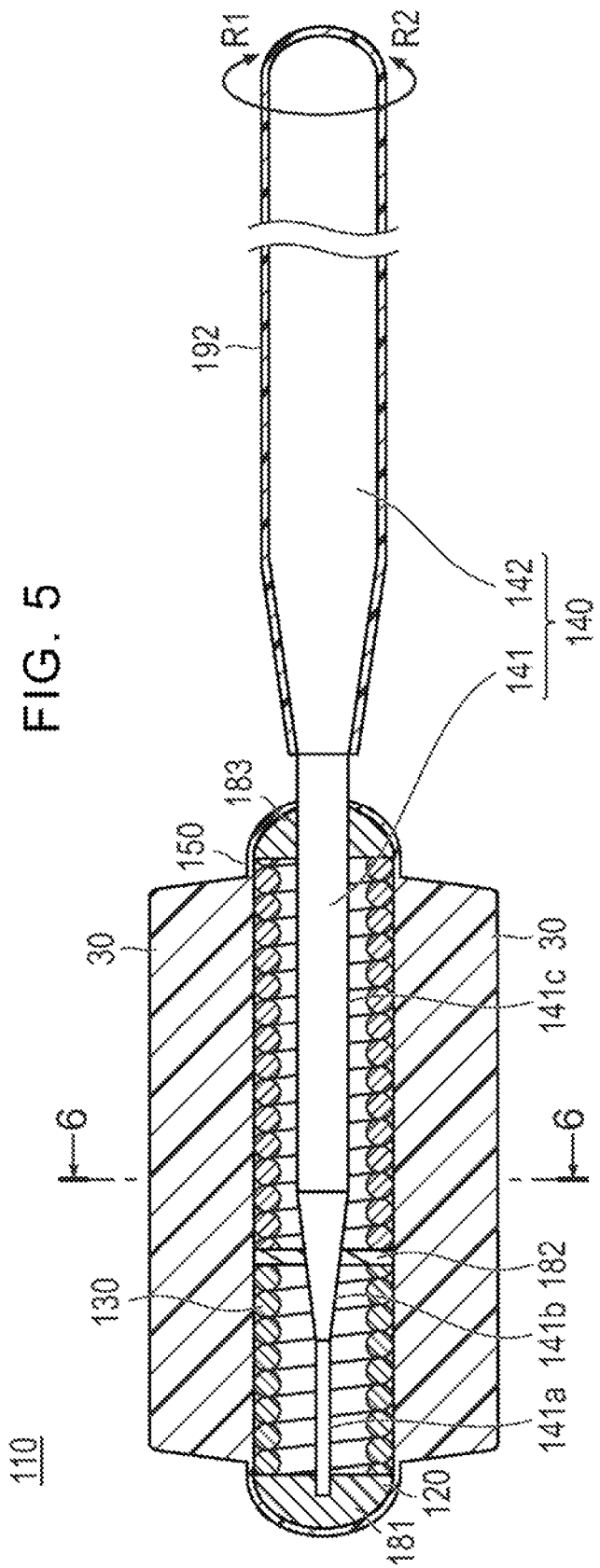

MEDICAL ELONGATED BODY

CROSS-REFERENCES TO RELATED APPLICATIONS

This application is based on and claims priority to Japanese Application No. JP2017-094095 filed on May 10, 2017, the entire content of which is incorporated herein by reference.

TECHNICAL FIELD

The present invention relates to a medical elongated body.

BACKGROUND ART

In the diagnosis or treatment of a lesion area inside a biological lumen, it is known to use medical elongated bodies such as guide wires and catheters. In such procedures, an operator inserts the medical elongated body into the biological lumen and then performs the treatment or diagnosis of the lesion area.

In order to enhance the insertion properties with respect to the inside of a biological lumen, a surface of such a medical elongated body is subjected to hydrophilic coating, fluorine coating, silicon coating, or the like to enhance its sliding properties. However, medical elongated bodies do not always require high sliding properties, for example, when performing a certain series of techniques of percutaneous coronary intervention (PCI). Furthermore, there are cases where low sliding properties are required, for example, to help prevent a medical elongated body from unintentionally moving from a target site in a biological lumen at which the medical elongated body is to be disposed.

For example, JP-A-2014-124408 discloses a guide wire in which a low-sliding portion is provided on a surface on a side opposite to a side on which a curved portion is curved. According to the guide wire configured as described above, it is possible to exhibit low sliding properties and to restrain the guide wire from unintentionally sliding at a target site inside a biological lumen. However, the provision of the low-sliding portion results in unfavorable insertion properties of the medical elongated body with respect to the inside of the biological lumen.

SUMMARY

An object of the present disclosure is to provide an improved medical elongated body which can be inserted into a biological lumen and can be restrained from unintentionally moving at a target site inside the biological lumen. In order to achieve these and other objects, there is provided a medical elongated body including a main body portion that extends in an axial direction, and a projection portion that is provided to protrude radially outward on an outer circumference of the main body portion and extends in the axial direction. One surface of the projection portion in a circumferential direction has higher sliding properties than the other surface of the projection portion in the circumferential direction.

According to the medical elongated body configured as described above, since the one surface of the projection portion is configured to have higher sliding properties than the other surface of the projection portion, the outer surface of the medical elongated body can exhibit sliding properties by rotating the medical elongated body to one side in the circumferential direction and deforming the projection portion such that the one surface of the projection portion is disposed on the outer surface of the medical elongated body. In addition, the outer surface of the medical elongated body can exhibit low sliding properties by rotating the medical elongated body to the other side in the circumferential direction and deforming the projection portion such that the other surface of the projection portion is disposed on the outer surface of the medical elongated body. Therefore, when the medical elongated body is introduced into a living body, the medical elongated body can be inserted into a biological lumen by inserting the medical elongated body while the medical elongated body is rotated to one side in the circumferential direction. In addition, the medical elongated body can be restrained from unintentionally moving at a target site by rotating the medical elongated body to the other side in the circumferential direction at the target site inside a biological lumen. From the above, it is possible to provide an improved medical elongated body which can be inserted into a biological lumen and can be restrained from unintentionally moving at a target site inside the biological lumen.

BRIEF DESCRIPTION OF THE DRAWINGS

FIG. 2(A) is a view illustrating a situation before projection portions are deformed, FIG. 2(B) is view illustrating a situation when the guide wire is rotated clockwise inside a biological lumen, and FIG. 2(C) is a view illustrating a situation when the guide wire is rotated counterclockwise inside a biological lumen.

FIG. 5 is a cross-sectional front view of a guide wire according to a second embodiment.

FIG. 6(A) is a view illustrating a situation before projection portion are deformed, FIG. 6(B) is a view illustrating a situation after the projection portions are deformed by rotating the guide wire clockwise inside a biological lumen, and FIG. 6(C) is a view illustrating a situation after the projection portions are deformed by rotating the guide wire counterclockwise inside a biological lumen.

DETAILED DESCRIPTION

Hereinafter, with reference to the accompanying drawings, exemplary embodiments will be described. Note that, the following disclosure does not limit the technical scope or meaning of the terms disclosed in the aspects. In addition, for the convenience of description, there are cases where the dimensional ratios of the drawings are exaggerated and are different from the actual ratios.

First Embodiment

Figure 1:
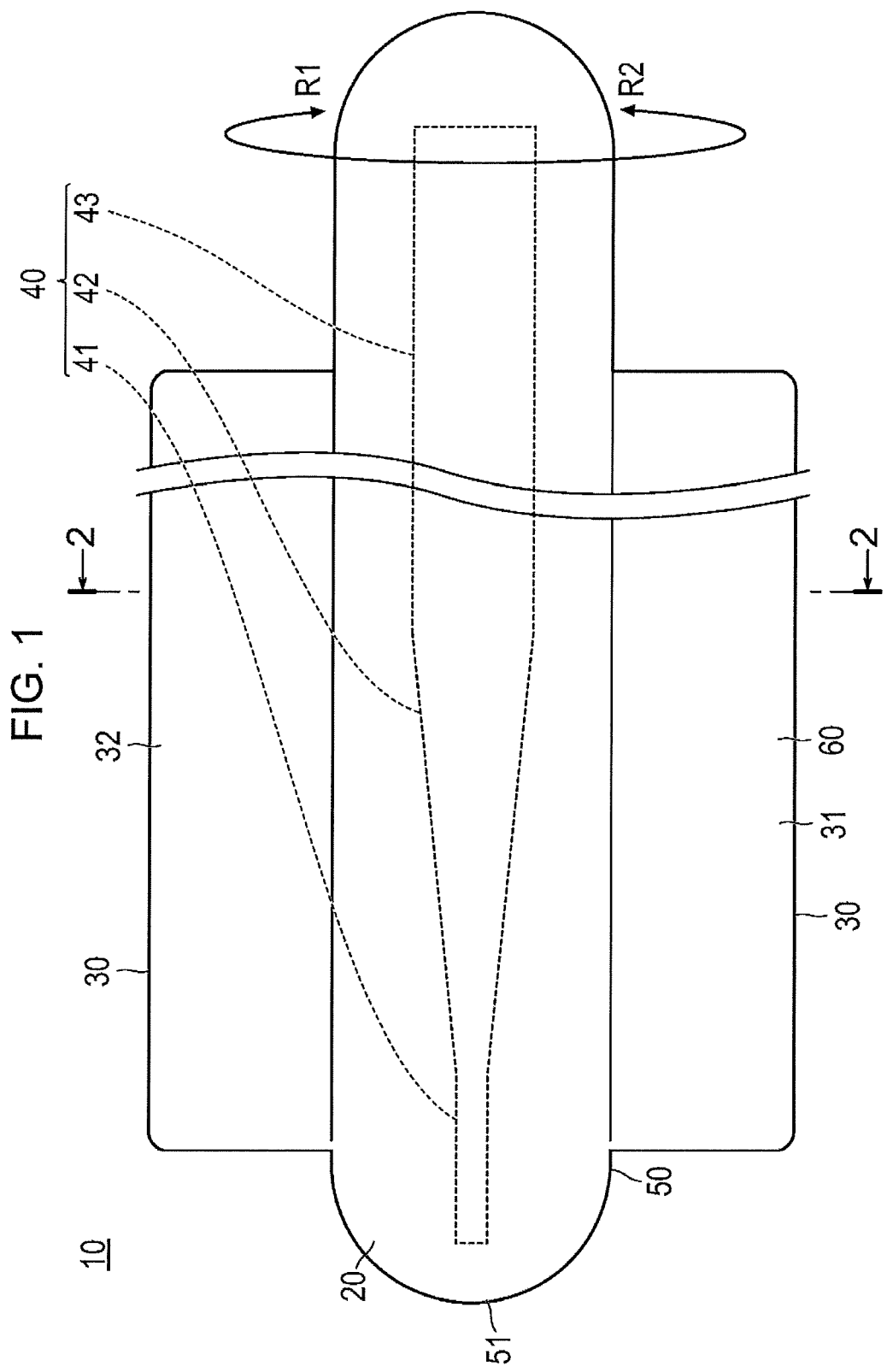
FIG. 1 is a front view of a guide wire according to a first embodiment.
Figure 2A:
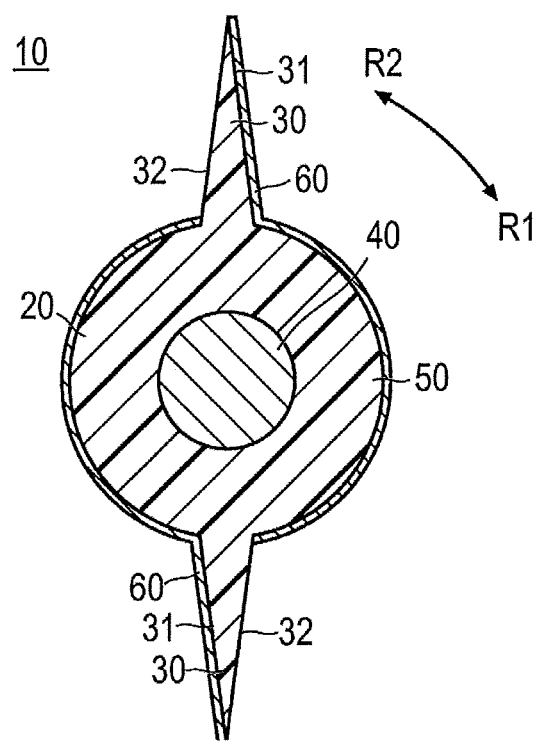
FIGS. 2(A), 2(B), and 2(C) are cross-sectional views taken along line 2-2 in FIG. 1.
Figure 2B:
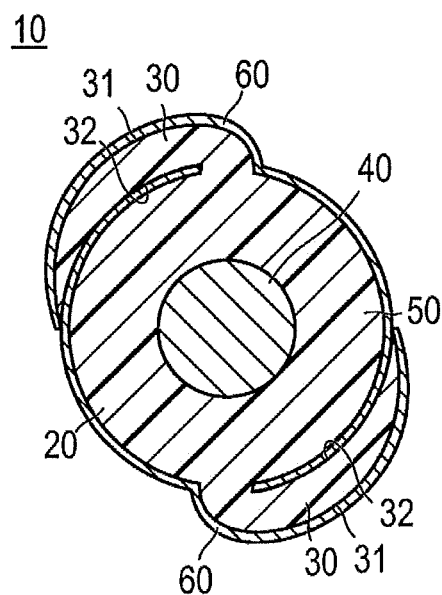
Figure 2C:
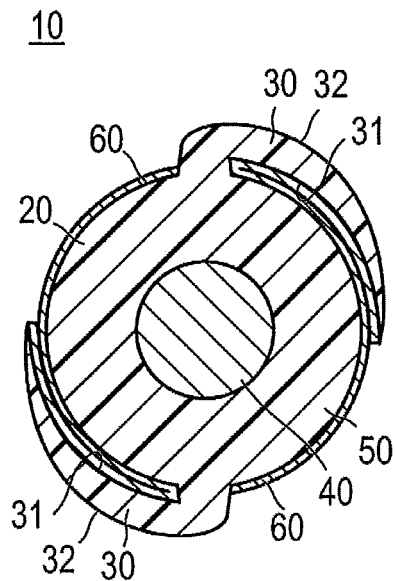

In the present embodiment, a guide wire 10 will be described as an example of a medical elongated body. FIG. 1 is a front view of a guide wire 10 according to a first embodiment. FIG. 2 is a cross-sectional view taken along line 2-2 in FIG. 1. FIG. 2(A) is a view illustrating a situation before projection portions 30 are deformed, FIG. 2(B) is a view illustrating a situation when the guide wire 10 is rotated clockwise inside a biological lumen, and FIG. 2(C) is a view illustrating a situation when the guide wire 10 is rotated counterclockwise inside a biological lumen.

In description of this specification, a direction in which the central axis of the guide wire 10 extends (transverse direction in FIG. 1) is defined as an "axial direction". In addition, a direction in which the guide wire 10 is operated to rotate around the axial direction is defined as a "circumferential direction".

In addition, in the guide wire 10, a side which is inserted into a living body (into a blood vessel) is defined as a distal side (left side in FIG. 1), and a side which on which a manual operation is performed by an operator positioned on a side opposite to the distal side is defined as a proximal side (right side in FIG. 1). In addition, in this specification, a distal portion denotes a part including a certain range in the axial direction from a distal end (outermost distal end), and a proximal portion denotes a part including a certain range in the axial direction from a proximal end (innermost proximal end).

In addition, a direction in which the guide wire 10 is rotated clockwise when seen from a hand side (proximal side) of an operator is indicated with an arrow R1 in each drawing, and a direction in which the guide wire 10 is rotated counterclockwise is indicated with an arrow R2 in each drawing.

As illustrated in FIGS. 1 and 2, the guide wire (corresponding to the medical elongated body) 10 according to the present embodiment has a main body portion 20 that extends in the axial direction, the projection portions 30 that are provided to protrude radially outward on an outer circumference of the main body portion 20 and extend in the axial direction, and a high-sliding layer 60 that is formed on the outermost circumference.

The length of the guide wire 10 along the axial direction is not particularly limited. For example, the length can range from 500 to 5,000 mm.

As illustrated in FIGS. 1 and 2, the main body portion 20 has a core wire 40 which extends in the axial direction, and a coating layer 50 which is provided to cover an outer surface of the core wire 40.

As illustrated in FIG. 1, the core wire 40 is constituted of one continuous wire having flexibility. The core wire 40 has a round bar portion 41 which is disposed on the distal side and having a constant outer diameter, a tapered portion 42 of which the outer diameter gradually increases from the round bar portion 41 toward the proximal side, and a constant outer diameter portion 43 which extends from the tapered portion 42 to the proximal side in a substantially constant outer diameter. Note that, the core wire 40 may have a flat plate-shaped flat plate portion in place of the round bar portion 41.

Note that, the shape of the core wire 40 is not limited to the illustrated shape. For example, the core wire 40 may be formed to have an outer shape constant from the distal side to the proximal side (constant outer diameter). In addition, for example, the core wire 40 may be constituted of a plurality of wires, instead of being constituted of one continuous wire.

A constituent material of the core wire 40 is not particularly limited. For example, a Ni—Ti-based alloy, stainless steel, a super elastic alloy, a piano wire, or a cobalt-based alloy can be used.

The coating layer 50 is configured to cover the core wire 40. It is preferable that a distal portion 51 of the coating layer 50 has a roundish shape as illustrated in FIG. 1, such that the inner wall of a biological lumen is not damaged.

A constituent material of the coating layer 50 is not particularly limited. It is preferable to use a material having relatively high flexibility. Examples thereof include polyolefin such as polyethylene and polypropylene; polyvinyl chloride, polyester (PET, PBT, and the like), polyamide, polyimide, polyurethane, polystyrene; polycarbonate, a silicone resin, a fluorine-based resin (PTFE, ETFE, PFA, and the like), and a composite material thereof; various rubber materials such as latex rubber and silicone rubber; and a composite material in which two or more thereof are combined. Among the materials described above, from a viewpoint of further improving flexibility, it is more preferable that a urethane-based resin is used. Accordingly, the distal portion of the guide wire 10 can have flexibility. Therefore, the inner wall of a biological lumen can be prevented from being damaged when the guide wire 10 is inserted into the biological lumen.

The thickness of the coating layer 50 is not particularly limited. For example, it is preferable that the thickness ranges from 10 to 800 μm. Note that, the coating layer 50 is not limited to a single-layer structure and may have a configuration in which a plurality of layers are stacked.

As illustrated in FIG. 2, the projection portions 30 are provided to protrude radially outward on the outer circumference of the coating layer 50. The projection portions 30 are configured to have a triangle shape reduced in width radially outward from the inside. However, the shape is not particularly limited. In the present embodiment, the projection portions 30 are integrally constituted with the coating layer 50. Therefore, the projection portions 30 are constituted of the same material as the coating layer 50. The projection portions 30 have flexibility to the extent that the projection portions 30 can be deformed as in FIG. 2(B) or 2(C) when the guide wire 10 is rotated inside a biological lumen.

In the present embodiment, as illustrated in FIG. 2, two projection portions 30 are provided at different positions in the circumferential direction. It is preferable that the two projection portions 30 are provided to be opposite to each other in the circumferential direction. That is, it is preferable that the two projection portions 30 are provided at intervals of 180 degrees in the circumferential direction. Note that, the number and the positions of projection portions 30 to be provided are not particularly limited.

As illustrated in FIGS. 2(B) and 2(C), it is preferable that the projection portions 30 are configured to cover at least half the outer surface of the coating layer 50 in the circumferential direction when the projection portions 30 are deformed in the circumferential direction to cover the coating layer 50. According to the guide wire 10 configured as described above, as illustrated in FIG. 2(C), the other surface 32 having low sliding properties can be formed on half or more of the outer surface of the guide wire 10 when the guide wire 10 is rotated to the counterclockwise R2 side inside a biological lumen. Therefore, the outer surface of the guide wire 10 can selectively exhibit low sliding properties. For example, in a case of the guide wire 10, it is preferable that the lengths of the projection portions 30 protruding radially outward from the outer circumference of the coating layer 50 range from 0.5 times to 1.0 time the outer diameter of the main body portion 20.

As illustrated in FIG. 1, the projection portions 30 are provided to extend in the axial direction. The positions at which the projection portions 30 are provided along the axial direction are not particularly limited. For example, in a case where the length of the guide wire 10 along the axial direction is 800 mm, it is possible to provide the projection portions 30 within a range from the position of 10 mm from the distal end of the coating layer 50 to the proximal side, to the position of 700 mm toward the proximal end.

For example, if the projection portions 30 are provided from the distal end of the coating layer 50, insertion properties of the guide wire 10 with respect to the inside of a biological lumen deteriorate. In contrast, in a case where the projection portions 30 are provided from the position of 10 mm from the distal end of the coating layer 50 to the proximal side, since no projection portion 30 is provided at the distal end of the guide wire 10, insertion properties of the guide wire 10 with respect to the inside of a biological lumen can be restrained from deteriorating.

In addition, for example, if the projection portions 30 are provided to the proximal end of the coating layer 50, since a region of the guide wire 10 gripped by an operator (region of the coating layer 50 excluding the projection portions 30) is narrowed, operability of the guide wire 10 for an operator deteriorates. In contrast, in a case where the projection portions 30 are provided in the range described above, since no projection portion 30 is provided at the proximal end of the guide wire 10, operability of the guide wire 10 for an operator can be restrained from deteriorating. In an alternative configuration, the projection portions 30 are provided from the distal end to the proximal end of the coating layer 50 along the axial direction.

The high-sliding layer 60 is provided in order to reduce frictional resistance between the guide wire 10 and the inner wall of a biological lumen or a catheter, to reduce tissue damage to a blood vessel and the like, and to improve operability for an operator. The high-sliding layer 60 is formed by being subjected to coating to have high sliding properties. As illustrated in FIG. 2(A), the high-sliding layer 60 is formed on a surface of one surface 31 on the clockwise R1 side in the circumferential direction in the projection portion 30 and the outer circumference of the coating layer 50. In addition, the high-sliding layer 60 is not provided on a surface of the other surface 32 on the counterclockwise R2 side in the circumferential direction in the projection portion 30. Therefore, the one surface 31 of the projection portion 30 has higher sliding properties than the other surface 32 of the projection portion 30. Note that, the degree of sliding properties can be evaluated by measuring a frictional resistance value of the surface using a known method such as a friction measuring instrument (Tribomaster TL201 Ts, manufactured by Trinity-Lab Inc.). When the frictional resistance value is significant, sliding properties are low, and when the frictional resistance value is small, sliding properties are high.

In the circumferential direction, a side (clockwise R1 side) on which the one surface 31 of one projection portion 30 (for example, the projection portion on the upper side in FIG. 2) is provided with respect to the other surface 32 is the same as a side (clockwise R1 side) on which the one surface 31 of another projection portion 30 (for example, the projection portion on the lower side in FIG. 2) is provided with respect to the other surface 32.

Therefore, as an operator rotates the guide wire 10 to the clockwise R1 side inside a biological lumen, the one surface 31 of each of the two projection portions 30 is disposed on the outer surface of the guide wire 10 due to friction with respect to the inner wall of the biological lumen, as illustrated in FIG. 2(B). As a result, the outer surface of the guide wire 10 is covered with the high-sliding layer 60, so that the outer surface of the guide wire 10 can selectively exhibit sliding properties. In addition, as an operator rotates the guide wire 10 to the counterclockwise R2 side inside a biological lumen, the other surface 32 of each of the two projection portions 30 is disposed on the outer surface of the guide wire 10 due to friction with respect to the inner wall of the biological lumen, as illustrated in FIG. 2(C). As a result, half or more of the outer surface of the guide wire 10 is covered with the other surface 32, so that the outer surface of the guide wire 10 can selectively exhibit low sliding properties.

A constituent material of the high-sliding layer 60 is not particularly limited. For example, it is possible to employ at least one selected from the group consisting of hydrophilic coating, fluorine coating, and silicon coating. As a material used in hydrophilic coating, for example, it is possible to employ a known hydrophilic substance such as a cellulose-based polymer substance, a polyethylene oxide-based polymer substance, a maleic anhydride-based polymer substance (for example, a maleic anhydride copolymer such as a methyl vinyl ether-maleic anhydride copolymer), an acrylamide-based polymer substance (for example, a block copolymer of polyacrylamide, polyglycidyl methacrylate-dimethyl acrylamide (PGMA-DMAA)), water-soluble nylon, polyvinyl alcohol, and polyvinylpyrrolidone. In addition, as a material used in fluorine coating, for example, it is possible to employ at least one selected from the group consisting of polytetrafluoroethylene (PTFE), a tetrafluoroethylene-perfluoroalkyl vinyl ether copolymer (PFA), polychlorotrifluoroethylene (PCTFE), polyvinylidene fluoride (PVDF), polyvinyl fluoride (PVF), a tetrafluoroethylene-hexafluoropropylene copolymer (FEP), and a tetrafluoroethylene-ethylene copolymer (PETFE). In addition, as a material used in silicon coating, for example, it is possible to employ silicone rubber and a silicone resin.

The thickness of the high-sliding layer 60 is not particularly limited. For example, it is preferable that the thickness ranges from 0.1 to 100 μm.

Figure 3:
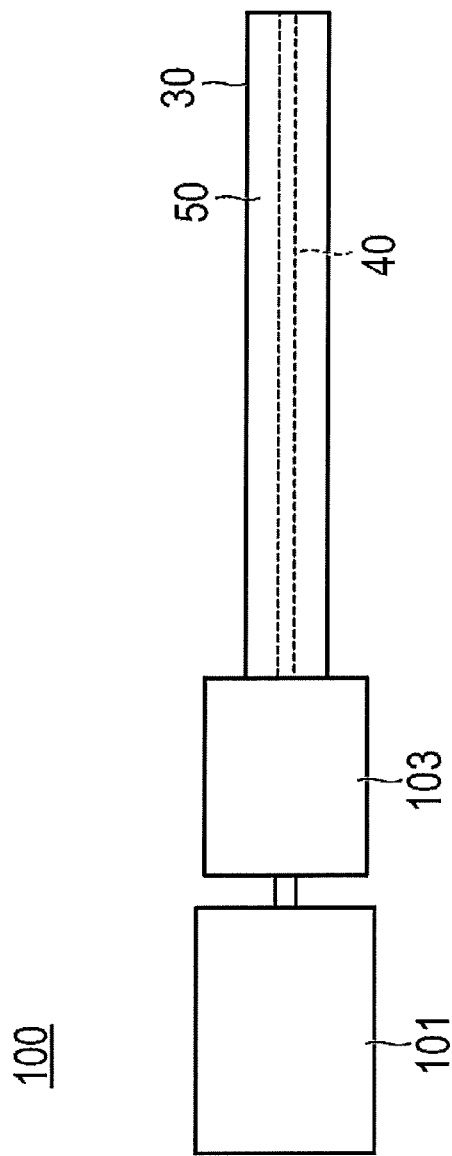
FIG. 3 is a schematic view illustrating an extrusion molding apparatus.

Next, a method of manufacturing the guide wire 10 will be described with reference to FIG. 3.

First, the material of the coating layer 50 is heated and melted. Using a known extrusion molding method, an intermediate product is formed by forming the coating layer 50, in which the projection portions 30 are formed, on the outer circumference of the core wire 40. An extrusion molding apparatus 100 illustrated in FIG. 3 is used in the extrusion molding method. The extrusion molding apparatus 100 has an extruder 101 for extruding a heat-melted material, and a mold 103 in which a resin is extruded by the extruder 101. The mold 103 includes concave portions (not illustrated) corresponding to the projection portions 30.

Next, as illustrated in FIG. 2(A), the high-sliding layer 60 is formed on the outer circumference of the core wire 40 with respect to the intermediate product covered with the coating layer 50 in which the projection portions 30 are formed, excluding the other surface 32 of the projection portion 30. A method of forming the high-sliding layer 60 is not particularly limited. For example, in a state where the other surface 32 is subjected to masking, the high-sliding layer 60 can be formed by coating the intermediate product with a material constituting the high-sliding layer 60. Otherwise, with respect to the intermediate product, in a state where the projection portions 30 are wound around the coating layer 50 such that the one surface 31 is disposed on the outer surface (refer to FIG. 2(B)), the high-sliding layer 60 can also be formed by coating the intermediate product with a material constituting the high-sliding layer 60. In this case, since the sites in the coating layer 50 covered with the projection portions 30 are not coated with the material constituting the high-sliding layer 60, for example, the sites can be coated with the material constituting the high-sliding layer 60 separately using predetermined coating means. In addition, in the case described above, the sites do not have to be coated with the material constituting the high-sliding layer 60 separately.

Next, with reference to FIGS. 2 and 4, an example of using the guide wire 10 according to the present embodiment will be described. Here, a technique in which a stent 200 indwells in a stenosed site N formed on the periphery of a bifurcated portion of a blood vessel (coronary artery) will be described as an example. In addition, here, an example, in which the guide wire 10 according to the present embodiment is applied to a technique of "wire protection" for preventing foreign bodies such as plaque included in the stenosed site N from moving to a lateral branch B2 of a blood vessel and occluding the lateral branch B2 of the blood vessel when the technique in which the stent 200 indwells on the periphery of a bifurcated portion of a blood vessel is performed, will be described.

First, an operator inserts a guide wire 400 for introducing a balloon catheter 300 into a main trunk B1 of a blood vessel. The operator introduces the guide wire 400 to the stenosed site N. Note that, as the guide wire 400, for example, it is possible to use a known guide wire used in treatment or the like of angiostenosis.

Next, the operator introduces the guide wire 10 according to the present embodiment from the main trunk B1 side of the blood vessel to the lateral branch B2 of the blood vessel. In this case, the operator introduces the guide wire 10 toward the distal side while rotating the guide wire 10 to the clockwise R1 side. As a result, as illustrated in FIG. 2(B), since the one surface 31 of the projection portion 30 is disposed on the outer surface of the guide wire 10, the outer surface of the guide wire 10 can selectively exhibit sliding properties, so that the guide wire 10 can be inserted into a blood vessel.

Figure 4:
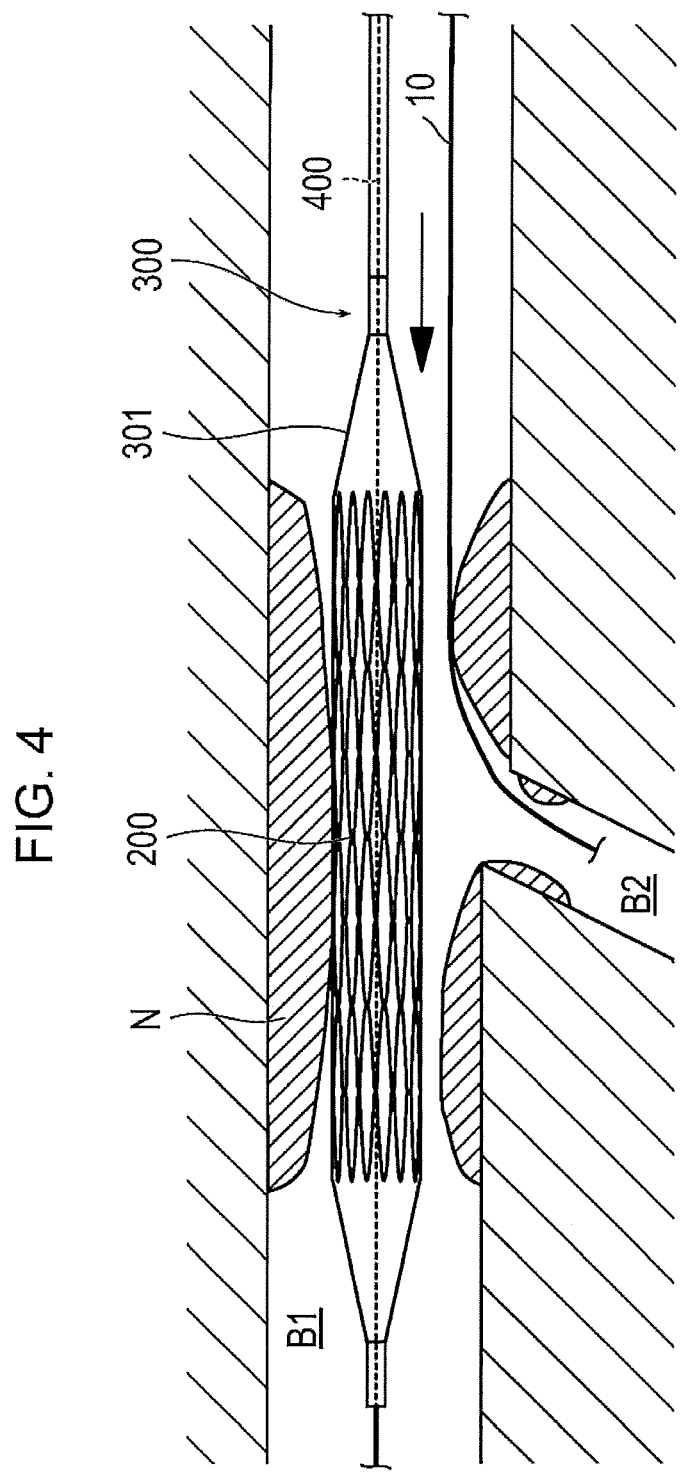
FIG. 4 is a view for describing an example of using the guide wire according to the first embodiment.

Next, as illustrated in FIG. 4, the operator introduces the balloon catheter 300 equipped with the stent 200 to the main trunk B1 of the blood vessel along the guide wire 400. The operator disposes the balloon catheter 300 in the stenosed site N. Then, the operator supplies a pressurizing medium to a balloon 301 of the balloon catheter 300 and causes the balloon 301 and the stent 200 to expand.

The guide wire 10 inserted into the lateral branch B2 of the blood vessel prevents plaque or the like included in the stenosed site N from moving to the lateral branch B2 of the blood vessel and occluding the lateral branch B2 when the balloon 301 and the stent 200 expand. In this case, the guide wire 10 is required to have low sliding properties not to unintentionally move in the lateral branch B2. Therefore, the operator rotates the guide wire 10 counterclockwise. As a result, as illustrated in FIG. 2(C), since the other surface 32 of the projection portion 30 is disposed on the outer surface of the guide wire 10, the outer surface of the guide wire 10 can exhibit low sliding properties. Thus, it is possible to restrain the guide wire 10 from unintentionally moving.

Next, the operator causes the balloon 301 to deflate and removes the balloon catheter 300 out of the living body. The stent 200 indwells inside the blood vessel in a state where the stenosed site N is dilated.

Next, the operator moves the guide wire 10 used in wire protection to the proximal side and removes the guide wire 10 out of the living body. In this case, the operator moves the guide wire 10 to the proximal side while rotating the guide wire 10 clockwise. As a result, as illustrated in FIG. 2(B), since the one surface 31 of the projection portion 30 is disposed on the outer surface of the guide wire 10, the outer surface of the guide wire 10 can selectively exhibit sliding properties, so that the guide wire 10 can be removed from the inside of the blood vessel.

Thereafter, the operator removes the guide wire 400 used for introducing the balloon catheter 300 out of the living body. Through the procedure as described above, an operator can cause the stent 200 to indwell on the periphery of the bifurcated portion of a blood vessel while performing wire protection.

As described above, the guide wire (medical elongated body) 10 according to the present embodiment has the main body portion 20 that extends in the axial direction, and the projection portions 30 that are provided to protrude radially outward on the outer circumference of the main body portion 20 and extend in the axial direction. The one surface 31 of the projection portion 30 in the circumferential direction has higher sliding properties than the other surface 32 of the projection portion 30 in the circumferential direction. According to the guide wire 10 configured as described above, since the one surface 31 of the projection portion 30 is configured to have higher sliding properties than the other surface 32 of the projection portion 30, the outer surface of the guide wire 10 can exhibit sliding properties by rotating the guide wire 10 to one side (clockwise R1 side) in the circumferential direction and deforming the projection portions 30 such that the one surface 31 of the projection portion 30 is disposed on the outer surface of the guide wire 10. In addition, the outer surface of the guide wire 10 can exhibit low sliding properties by rotating the guide wire 10 to the other side (counterclockwise R2 side) in the circumferential direction and deforming the projection portions 30 such that the other surface 32 of the projection portion 30 is disposed on the outer surface of the guide wire 10. Therefore, when the guide wire 10 is introduced into a living body, the guide wire 10 can be inserted into a biological lumen by inserting the guide wire 10 while the guide wire 10 is rotated to one side (clockwise R1 side) in the circumferential direction. In addition, the guide wire 10 can be restrained from unintentionally moving at a target site by rotating the guide wire 10 to the other side (counterclockwise R2 side) in the circumferential direction at the target site inside a biological lumen. From above, it is possible to provide a guide wire 10 which can be inserted into a biological lumen and can be restrained from unintentionally moving at a target site inside the biological lumen.

In addition, a plurality of the projection portions 30 are provided at different positions in the circumferential direction. In the circumferential direction, a side (clockwise R1 side) on which the one surface 31 of one of the projection portions 30 is provided with respect to the other surface 32 is the same as a side (clockwise R1 side) on which the one surface 31 of another one of the projection portions 30 is provided with respect to the other surface 32. According to the guide wire 10 configured as described above, when the guide wire 10 is rotated in the circumferential direction, since surfaces of the plurality of projection portions 30 having the same properties (sliding properties or low sliding properties) are formed on the outer surface, it is possible to selectively exhibit sliding properties or low sliding properties.

In addition, the projection portions 30 are configured to cover at least half the outer surface of the coating layer 50 in the circumferential direction when the projection portions 30 are deformed in the circumferential direction to cover the coating layer 50. According to the guide wire 10 configured as described above, as illustrated in FIG. 2(C), the other surface 32 having low sliding properties can be formed on half or more of the outer surface of the guide wire 10 when the guide wire 10 is rotated counterclockwise inside a biological lumen. Therefore, the outer surface of the guide wire 10 can selectively exhibit low sliding properties.

In addition, the plurality of projection portions 30 are provided at different positions in the circumferential direction, and the plurality of projection portions 30 are provided to be opposite to each other in the circumferential direction. According to the guide wire 10 configured as described above, as illustrated in FIG. 2(C), since the other surface 32 is formed on the outer surface at the opposite location in the circumferential direction and can exhibit low sliding properties, the guide wire 10 can exhibit well-balanced low sliding properties throughout the entire circumferential direction. Thus, the guide wire 10 can be more strongly restrained from unintentionally moving at a target site.

In addition, two projection portions 30 are provided at different positions in the circumferential direction. According to the guide wire 10 configured as described above, the configuration of the mold 103 can be simplified compared to a guide wire including three or more projection portions 30.

In addition, the high-sliding layer 60 subjected to coating to have high sliding properties selected from hydrophilic coating, fluorine coating, and silicon coating is formed on the one surface 31. According to the guide wire 10 configured as described above, the one surface 31 exhibits sliding properties.

In addition, the other surface 32 is subjected to no coating. According to the guide wire 10 configured as described above, since a step of coating the other surface 32 is no longer necessary, manufacturing is facilitated. In addition, the other surface 32 exhibits low sliding properties.

Second Embodiment

Next, with reference to FIGS. 5 and 6, a configuration of a guide wire 110 according to a second embodiment will be described.

Figure 6A:
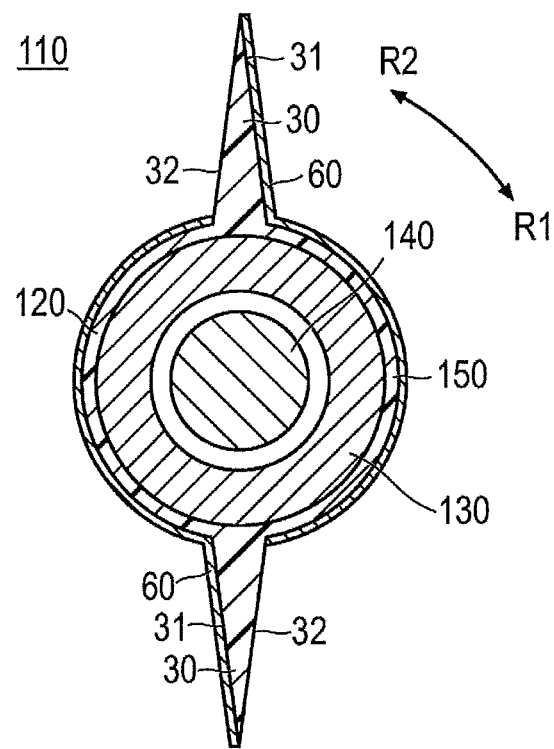
FIGS. 6(A), 6(B), and 6(C) are cross-sectional views taken along line 6-6 in FIG. 5.
Figure 6B:
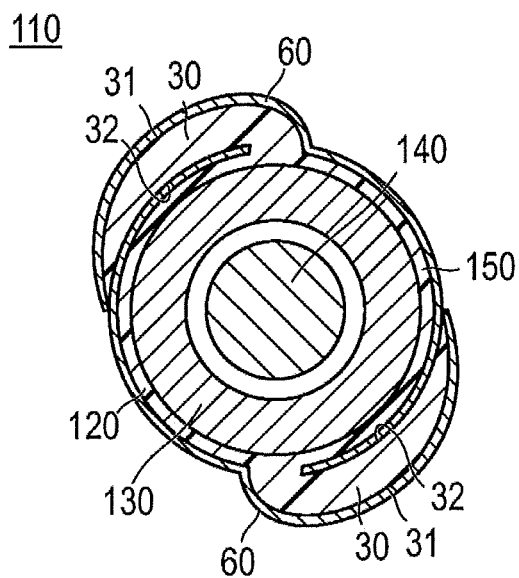
Figure 6C:
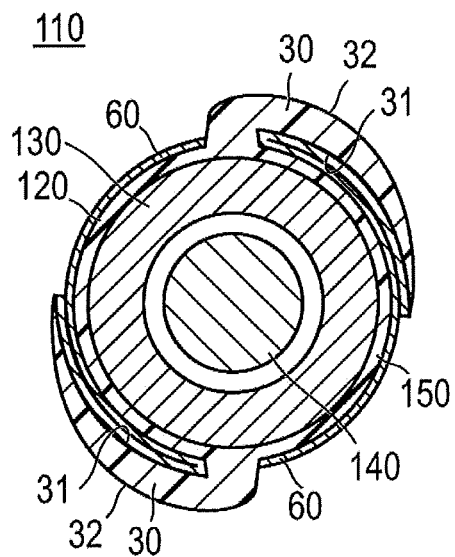

FIG. 5 is a cross-sectional front view of the guide wire 110 according to the second embodiment. FIG. 6 is a cross-sectional view taken along line 6-6 in FIG. 5. FIG. 6(A) is a view illustrating a situation before the projection portions 30 are deformed, FIG. 6(B) is a view illustrating a situation after the projection portions 30 are deformed by rotating the guide wire 110 clockwise inside a biological lumen, and FIG. 6(C) is a view illustrating a situation after the projection portions 30 are deformed by rotating the guide wire 110 counterclockwise inside a biological lumen. Description of parts common to the first embodiment will be omitted, and characteristic points in only the second embodiment will be described. Note that, the same reference signs are applied to the same members as those of the first embodiment described above, and overlapping description will be omitted. Compared to the first embodiment, the second embodiment differs in being provided with a coil portion 130.

As illustrated in FIGS. 5 and 6, the guide wire 110 according to the second embodiment includes a main body portion 120 that extends in the axial direction, the projection portions 30 that are provided to protrude radially outward on the outer circumference of the main body portion 120 and extend in the axial direction, and the high-sliding layer 60 formed on the outermost circumference. Since the configurations of the projection portions 30 and the high-sliding layer 60 are similar to those of the first embodiment, description will be omitted.

As illustrated in FIGS. 5 and 6, the main body portion 120 has a core wire 140 that extends in the axial direction, the coil portion 130 that is disposed to cover at least the distal portion of the core wire 140, and a coating layer 150 that is provided to cover the coil portion 130.

As illustrated in FIG. 5, the core wire 140 has a first core portion 141 which is disposed on the distal side in the axial direction, and a second core portion 142 which is disposed on the proximal side of the first core portion 141 and is joined to the first core portion 141.

The first core portion 141 has a round bar portion 141a which is disposed on the distal side and has a constant outer diameter, a tapered portion 141b which extends from the round bar portion 141a to the proximal side, and a constant outer diameter portion 141c which extends from the tapered portion 141b to the proximal side in a substantially constant outer diameter. Note that, the shape of the first core portion 141 is not limited to the illustrated shape. For example, the first core portion 141 may be formed to have an outer shape constant from the distal side to the proximal side (constant outer diameter). In addition, for example, the core wire 140 may be constituted of one continuous member, instead of being constituted of a plurality of members such as the first core portion 141 and the second core portion 142.

A constituent material of the first core portion 141 is not particularly limited. For example, a Ni—Ti-based alloy, stainless steel, or a super elastic alloy can be used. In addition, a constituent material of the second core portion 142 is not particularly limited as along as the constituent material thereof is different from the constituent material of the first core portion 141. For example, stainless steel or a cobalt-based alloy can be used. For example, the first core portion 141 and the second core portion 142 can be joined to each other by a method such as welding.

The coil portion 130 is disposed to cover a certain range of the first core portion 141 in the axial direction. The coil portion 130 is constituted of a wire spirally wound along the core wire 140 in the circumferential direction while having the core wire 140 as the center.

The inner diameter and the outer diameter of the coil portion 130 are formed to be substantially constant along the axial direction. Note that, the length, the outer diameter, and the inner diameter of the coil portion 130 along the axial direction are not particularly limited and can be suitably set in accordance with the product specification or the like of the guide wire 110.

The distal portion of the coil portion 130 is fixed to a location in the vicinity of the distal portion of the first core portion 141 via a first fixing portion 181. An intermediate portion of the coil portion 130 in the axial direction is fixed to a location in the vicinity of the middle of the first core portion 141 via a second fixing portion 182. The proximal portion of the coil portion 130 is fixed to a location in the vicinity of the proximal portion of the first core portion 141 via a third fixing portion 183. For example, each of the fixing portions 181, 182, and 183 can be constituted using a solder, a brazing filler metal, and an adhesive. It is preferable that a distal surface of the first fixing portion 181 has a roundish shape as illustrated, in consideration of an influence to a biological lumen such as a blood vessel.

A constituent material of a wire forming the coil portion 130 is not particularly limited. For example, it is possible to use a metal such as stainless steel, a super elastic alloy, a cobalt-based alloy, gold, platinum, and tungsten, or an alloy including thereof. In the coil portion 130, for example, the distal portion and the proximal portion can be constituted of materials different from each other. For example, the distal portion of the coil portion 130 can be constituted of a radiopaque material, and the proximal portion of the coil portion 130 can be constituted of a material which is likely to transmit an X-ray compared to the distal portion of the coil portion 130.

As illustrated in FIG. 6, the coating layer 150 is provided on the outer surface of the coil portion 130. The coating layer 150 has substantially the same configuration as the coating layer 50 of the first embodiment described above.

A resin coating layer 192 is provided on the outer surface of the second core portion 142. For example, the resin coating layer 192 can be formed of a fluorine-based resin such as PTFE and ETFE.

According to the guide wire 110 formed as described above, as an operator rotates the guide wire 110 clockwise inside a biological lumen, the projection portions 30 are deformed and the one surface 31 of the projection portion 30 is disposed on the outer surface of the guide wire 110 due to friction with respect to the inner wall of the biological lumen, as illustrated in FIG. 6(B). As a result, the outer surface of the guide wire 110 is covered with the high-sliding layer 60, so that the outer surface of the guide wire 110 exhibits sliding properties. In addition, as an operator rotates the guide wire 110 counterclockwise inside a biological lumen, the projection portions 30 are deformed and the other surface 32 of the projection portion 30 is disposed on the outer surface of the guide wire 110 due to friction with respect to the inner wall of the biological lumen, as illustrated in FIG. 6(C). As a result, half or more of the outer surface of the guide wire 110 is covered with the other surface 32, so that the outer surface of the guide wire 110 exhibits low sliding properties.

Hereinabove, exemplary embodiments of guide wires according to the present disclosure have been described. However, the present invention is not limited to the configurations described in the embodiments.

Figure 7:
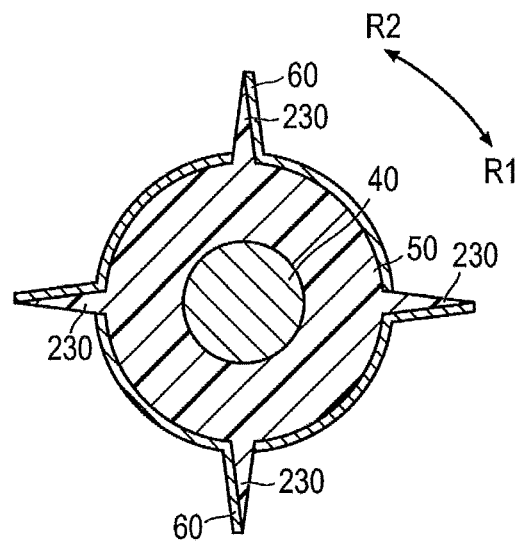
FIG. 7 is a view of a guide wire according to Modification Example 1 corresponding to FIG. 2(A).

For example, in the embodiments described above, two projection portions 30 are provided at different positions in the circumferential direction. However, as illustrated in FIG. 7, four projection portions 230 may be provided. In this case, in order to cover half the outer surface of the coating layer 50, the lengths of the projection portions 230 protruding radially outward can be half the lengths of the projection portions 30 of the guide wire 10 protruding radially outward according to the embodiments described above. Therefore, operability of the guide wire is improved.

Figure 8:
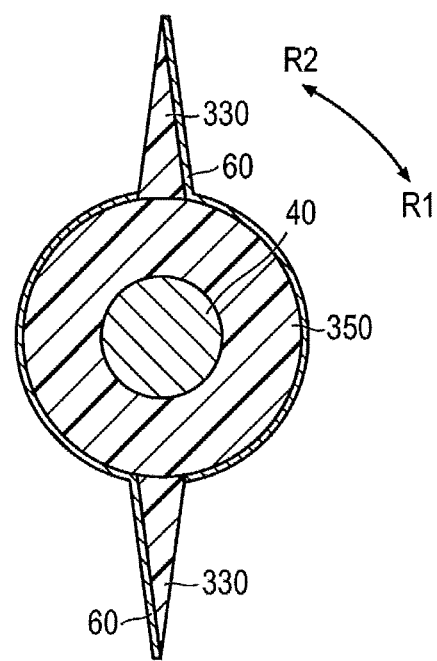
FIG. 8 is a view of a guide wire according to Modification Example 2 corresponding to FIG. 2(A).

In addition, in the embodiments described above, the projection portions 30 are integrally constituted with the coating layer 50. However, as illustrated in FIG. 8, projection portions 330 may be constituted as bodies separate from a coating layer 350. In this case, the projection portions 330 can be bonded to the coating layer 350 using an adhesive, for example.

Figure 9:
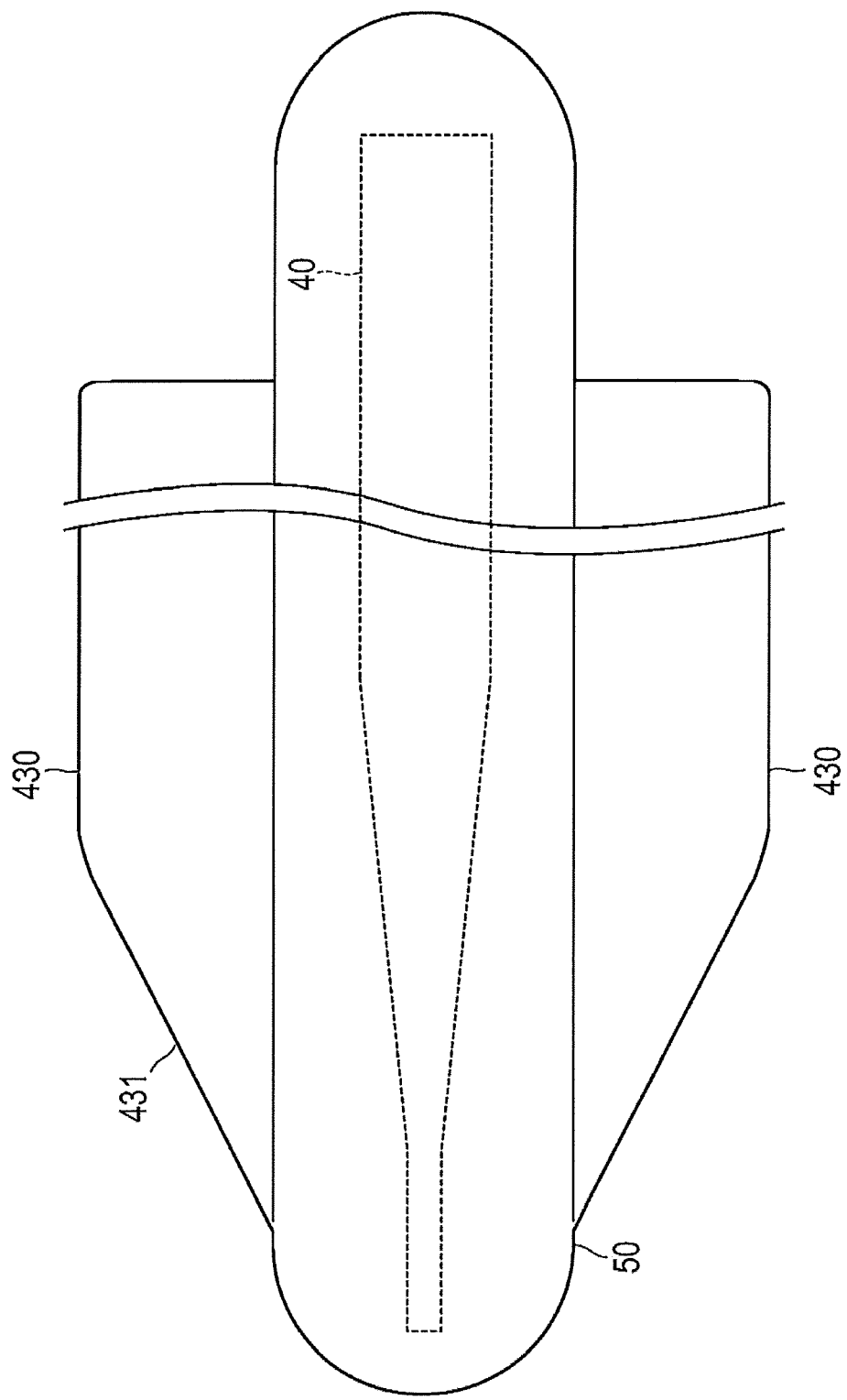
FIG. 9 is a view of a guide wire according to Modification Example 3 corresponding to FIG. 1.

In addition, in the embodiments described above, the projection portions 30 are constituted such that the outer diameter becomes substantially constant along the axial direction. However, as illustrated in FIG. 9, projection portions 430 may have tapered portions 431 in which the radially protruding length gradually increases from the distal side toward the proximal side. According to the guide wire configured as described above, passing properties of the guide wire with respect to the inside of a biological lumen can be improved.

Figure 10:
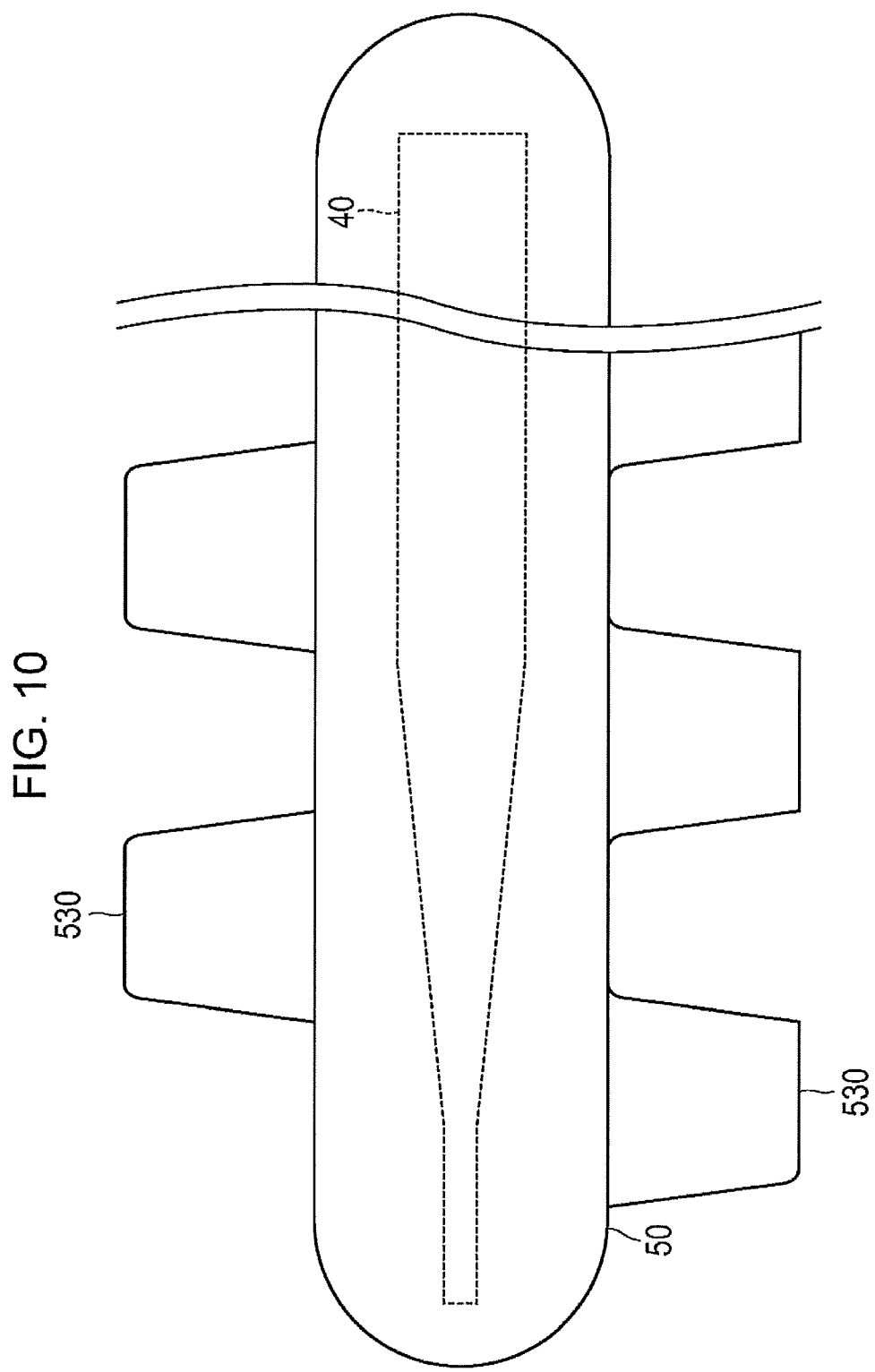
FIG. 10 is a view of a guide wire according to Modification Example 4 corresponding to FIG. 1.

In addition, in the embodiments described above, two projection portions 30 are continuously formed along the axial direction and are provided at different positions in the circumferential direction. However, upper and lower projection portions 530 illustrated in FIG. 10 may be intermittently constituted along the axial direction to be alternately provided in the axial direction. In this case, the projection portions 530 are constituted as bodies separate from the coating layer 50. According to the guide wire configured as described above, compared to the configuration in which two projection portions are continuously formed along the axial direction and are provided at different positions in the circumferential direction, the outer diameter becomes small in a cross section orthogonal to the axial direction. Therefore, passing properties of the guide wire with respect to the inside of a biological lumen can be improved.

Figure 11:
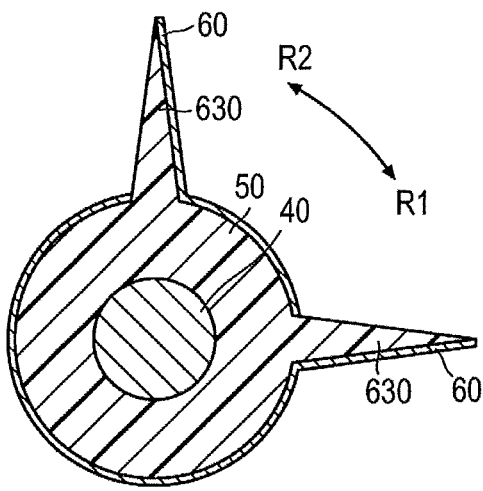
FIG. 11 is a view of a guide wire according to Modification Example 5 corresponding to FIG. 2(A).

In addition, in the embodiments described above, the two projection portions 30 provided at positions different from each other in the circumferential direction are formed at positions opposite to each other in the circumferential direction. However, as illustrated in FIG. 11, two projection portions 630 provided at positions different from each other in the circumferential direction may be formed at positions not opposite to each other in the circumferential direction.

Figure 12:
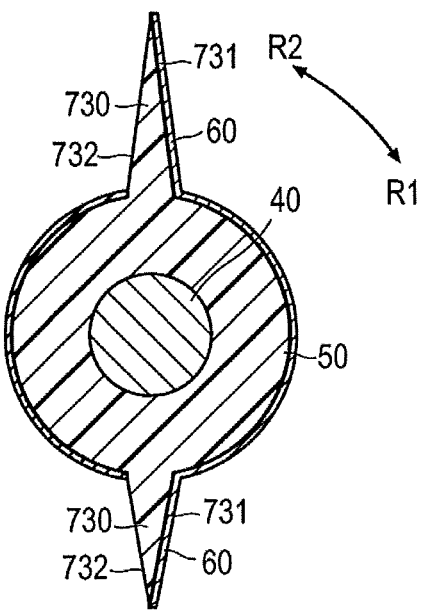
FIG. 12 is a view of a guide wire according to Modification Example 6 corresponding to FIG. 2(A).

In addition, in the embodiments described above, in the circumferential direction, a side (clockwise R1 side) on which the one surface 31 of one projection portion 30 is provided with respect to the other surface 32 is the same as a side (clockwise R1 side) on which the one surface 31 of another projection portion 30 is provided with respect to the other surface 32. However, as illustrated in FIG. 12, a side (clockwise R1 side) on which one surface 731 of one projection portion 730 (projection portion on the upper side in the drawing) is provided with respect to the other surface 732 may be different from a side (counterclockwise R2 side) on which the one surface 731 of another projection portion 730 (projection portion on the lower side in the drawing) is provided with respect to the other surface 732. In this case, it is preferable that the lengths of one projection portion 730 and another projection portion 730 protruding radially outward are different from each other. As a result, when the guide wire in FIG. 12 is rotated to the counterclockwise R2 side inside a biological lumen, compared to when being rotated to the clockwise R1 side, the rate of the other surface 732 having low sliding properties and covering the outer surface of the guide wire increases. Thus, compared to when being rotated to the clockwise R1 side, the guide wire of FIG. 12 can exhibit low sliding properties when being rotated to the counterclockwise R2 side. In other words, compared to when being rotated to the counterclockwise R2 side, the area covered with the other surface 732 having low sliding properties is reduced, so that the guide wire of FIG. 12 can exhibit high sliding properties when being rotated to the clockwise R1 side.

Figure 13:
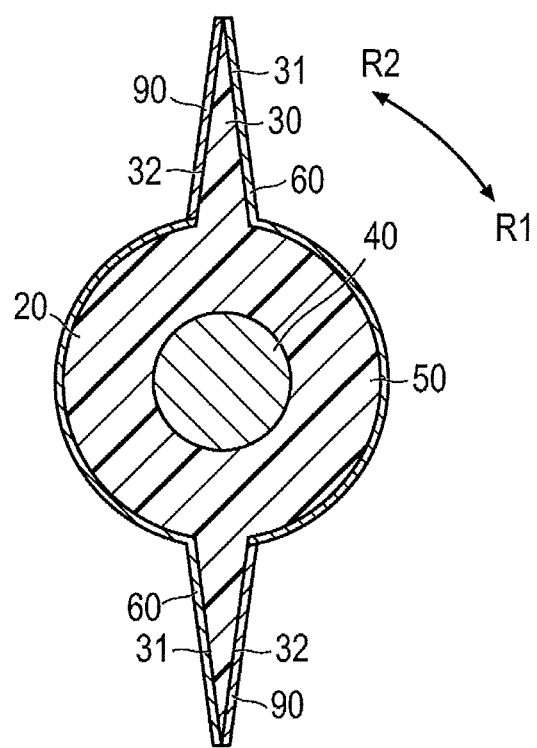
FIG. 13 is a view of a guide wire according to Modification Example 7 corresponding to FIG. 2(A).

In addition, in the embodiments described above, the other surface 32 of the projection portion 30 is subjected to no coating. However, as illustrated in FIG. 13, a low-sliding layer 90 subjected to coating to have lower sliding properties than the high-sliding layer 60 formed on the surface of the one surface 31 may be formed on the other surface 32 of the projection portion 30. A constituent material of the low-sliding layer 90 is not particularly limited. For example, a hydrophobic material can be employed. Examples of the hydrophobic material include polytetrafluoroethylene (PTFE), fluorinated ethylene propylene (FEP), reactive curable silicone, or a substance having small surface free energy being terminated with an alkyl group or a perfluoroalkyl group.

In addition, in the embodiments described above, the one surface 31 is configured to have higher sliding properties than the other surface 32 by causing the one surface 31 to be subjected to coating to have high sliding properties and causing the other surface 32 to be subjected to no coating. However, the configuration is not particularly limited as long as the one surface 31 is configured to have higher sliding properties than the other surface 32. For example, a surface treatment portion may be formed by performing surface treatment such as blast treatment with respect to the other surface 32, such that the other surface 32 has low sliding properties. As a result, the one surface 31 has higher sliding properties than the other surface 32.

In addition, in the embodiments described above, the projection portions 30 are configured to cover half the coating layer 50 when the guide wire 10 is rotated. However, the projection portions may be configured to cover less than half or more than half the coating layer 50 when the guide wire is rotated.

In addition, a guide wire has been described as an example of a medical elongated body. However, the present invention is not limited to a guide wire and can also be, for example, a catheter serving as an elongated member.

What is claimed is:

1. A guide wire comprising:
   a core wire that extends in an axial direction; and
   a single coating layer which covers an outer surface of said core wire and defines an outer wall, wherein
   the single coating layer includes a projection portion which protrudes radially outward from the outer wall and extends in the axial direction, and
   one surface of the projection portion in a circumferential direction has lower sliding resistance than an other surface of the projection portion in the circumferential direction.

2. The guide wire according to claim 1,
   wherein a plurality of the projection portions are provided at different positions in the circumferential direction, and
   wherein in the circumferential direction, the one surface of one of the plurality of the projection portions and the one surface of an other one of the plurality of the projection portions both face one of clockwise or counterclockwise, and the other surface of the one of the plurality of the projection portions and the other surface of the other one of the plurality of the projection portions both face the other of clockwise or counterclockwise.

3. The guide wire according to claim 1,
   wherein the projection portion is configured to cover at least half an outer surface of the outer wall in the circumferential direction when the projection portion is deformed in the circumferential direction to cover the outer surface of the outer wall.

4. The guide wire according to claim 1,
   wherein a plurality of the projection portions are provided at different positions in the circumferential direction, and
   wherein the plurality of projection portions are provided to be equally spaced from each other in the circumferential direction.

5. The guide wire according to claim 1,
   wherein two projection portions are provided at different positions in the circumferential direction.

6. The guide wire according to claim 1,
   wherein a coating selected from hydrophilic coating, fluorine coating, and silicon coating is formed on the one surface.

7. The guide wire according to claim 6,
   wherein a coating having higher sliding resistance than the coating formed on the one surface is formed on the other surface, or the other surface is subjected to no coating.

8. The guide wire according to claim 1,
   wherein a surface treatment portion subjected to surface treatment to have higher sliding resistance than the one surface is formed on the other surface.

9. A method of using a guide wire, the method comprising:
   preparing a guidewire, the guide wire including a core wire which extends in an axial direction and a single coating layer which covers an outer surface of said core wire and defines an outer wall, wherein the single coating layer includes a projection portion which protrudes radially outward from the outer wall and extends in the axial direction, and one surface of the projection portion in a circumferential direction has lower sliding resistance than an other surface of the projection portion in the circumferential direction, and
   changing sliding properties of an outer surface of the guide wire by rotating the guide wire such that the one surface of the projection portion or the other surface of the projection portion is disposed on the outer surface of the guide wire.

10. The method of using the guide wire according to claim 9, wherein the changing of the sliding properties of the outer surface comprises deforming the projection portion by rotating the guide wire.

11. The method of using the guide wire according to claim 9, wherein a plurality of the projection portions are provided at different positions in the circumferential direction, and
   wherein the changing of the sliding properties of the outer surface comprises deforming the plurality of the projection portions by rotating the guide wire.

12. A guide wire comprising:
   a core wire that extends in an axial direction; and
   a single coating layer which covers an outer surface of said core wire and defines an outer wall, wherein
   the single coating layer includes a projection portion that covers the outer wall and extends in the axial direction,
   the projection portion has one surface and an other surface in a circumferential direction, and
   wherein a frictional resistance value of the one surface and a frictional resistance value of the other surface are different from each other.

13. The guide wire according to claim 12,
   wherein a plurality of the projection portions are provided at different positions in the circumferential direction, and
   wherein in the circumferential direction, the one surface of one of the plurality of the projection portions and the one surface of an other one of the plurality of the projection portions both face one of clockwise or counterclockwise, and the other surface of the one of the plurality of the projection portions and the other surface of the other one of the plurality of the projection portions both face the other of clockwise or counterclockwise.

14. The guide wire according to claim 12,
wherein the projection portion is configured to cover at least half an outer surface of the outer wall in the circumferential direction when the projection portion is deformed in the circumferential direction to cover the outer surface of the outer wall.

15. The guide wire according to claim 12,
wherein a plurality of the projection portions are provided at different positions in the circumferential direction, and
wherein the plurality of projection portions are provided to be equally spaced from each other in the circumferential direction.

16. The guide wire according to claim 12,
wherein two projection portions are provided at different positions in the circumferential direction.

\* \* \* \* \*